(12) United States Patent
Cianciosi

(10) Patent No.: US 6,652,141 B1
(45) Date of Patent: Nov. 25, 2003

(54) INTRAORAL SENSOR

(75) Inventor: Egidio Cianciosi, Scottsdale, AZ (US)

(73) Assignee: Cygnus Technologies, L.L.C., Scottsdale, AZ (US)

( * ) Notice: Subject to any disclaimer, the term of this patent is extended or adjusted under 35 U.S.C. 154(b) by 0 days.

(21) Appl. No.: 10/056,419

(22) Filed: Jan. 24, 2002

(51) Int. Cl.[7] .............................................. A61B 6/14
(52) U.S. Cl. ........................ 378/191; 378/38; 378/98.8
(58) Field of Search ........................ 378/38, 98.8, 168, 378/189, 191

(56) References Cited

U.S. PATENT DOCUMENTS

| | | | | |
|---|---|---|---|---|
| 3,851,178 A | * | 11/1974 | Borden | 378/169 |
| 4,160,997 A | | 7/1979 | Schwartz | 348/66 |
| 5,285,491 A | * | 2/1994 | Muylle et al. | 378/168 |
| 5,434,418 A | | 7/1995 | Schick | 250/370.11 |
| 5,510,623 A | * | 4/1996 | Sayag et al. | 250/370.11 |
| 6,169,781 B1 | * | 1/2001 | Doebert et al. | 378/98.8 |
| 6,309,101 B1 | * | 10/2001 | Bacchetta et al. | 378/169 |
| 6,320,934 B1 | * | 11/2001 | Carroll et al. | 378/98.8 |

* cited by examiner

Primary Examiner—Drew A. Dunn
Assistant Examiner—Allen C. Ho
(74) Attorney, Agent, or Firm—Lawrence R. Oremland, P.C.

(57) ABSTRACT

A new and improved intraoral sensor for use in a filmless radiography system is disclosed. The sensor is configured to fit comfortably and close to a target area in an intraoral cavity. By providing a comfortable relative fit to the target area, the sensor is ergonomically improved, in terms of its comfort and feel to a dental patient. In addition, the configuration of the sensor is designed to allow the sensor to be placed closer to a target area in an oral cavity than prior sensors (i.e. closer to target teeth, gum, etc). Moreover, the sensor is configured so that it can easily be located in a correct position relative to the target area, and when located correctly to properly position its sensing structure for receiving radiant energy. These features are believed to reduce refractive error in the image received by the sensor, thereby improving the image data transmitted by the sensor.

4 Claims, 3 Drawing Sheets

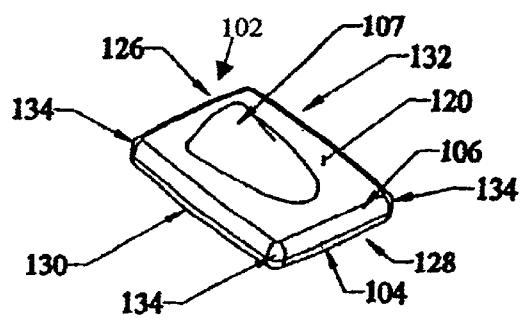
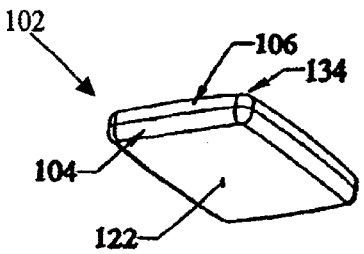
FIG. 1  FIG. 2
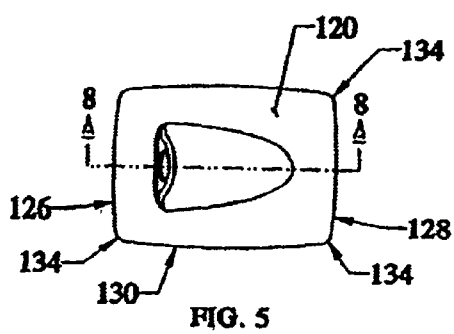
FIG. 5
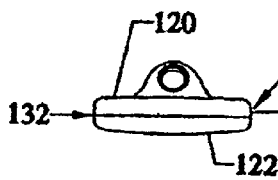
FIG. 4
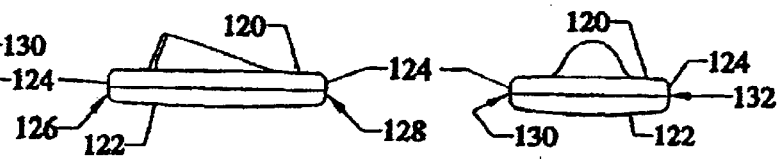
FIG. 7   FIG. 3
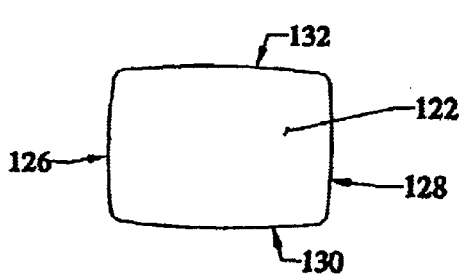
FIG. 6

INTRAORAL SENSOR

TECHNICAL FILED

The present invention relates to an intraoral sensor designed for use in a filmless radiography system.

BACKGROUND

Dentists and oral surgeons typically use x-radiation ("x-rays") to obtain images of their patients' teeth, mouths and gums to aid in diagnosis and treatment. In traditional oral and dental radiography, a cartridge containing a piece of photographic film is placed in the patient's mouth, for example behind a patient's tooth, and an x-ray beam is projected through the tooth and onto the film. The film, after being exposed in this manner, is developed in a dark room or a closed processor using special chemicals to obtain a photographic image of the tooth.

More recently, the field of filmless dental radiography has emerged. In filmless dental radiography, an x-ray beam is still projected through the patient's tooth, but no photographic film is used. Instead, an electronic sensor is placed in the patient's mouth behind the tooth to be examined. The electronic sensor may include a charge-coupled device (CCD) or any other filmless radiation sensor. The x-rays pass through the tooth and impinge on the electronic sensor, which converts the x-rays into an electrical signal. The electrical signal is transmitted over a wire to a computer, either directly or though a module containing intermediate processing circuitry. The computer then processes the signal to produce an image on an associated output device, such as a monitor or a printer.

Filmless dental radiography offers several advantages over traditional film-based radiography. Most importantly, the electronic sensor is much more sensitive to x-rays than is film, allowing the dosage of x-rays to the patient to be lowered by as much as 90%. Also, the image of the tooth is generated by the computer almost instantaneously, thus eliminating the entire developing process, including the use of potentially harmful chemicals. In addition, because the images are generated electronically, they can be stored electronically in a computer database. Examples of filmless dental radiography systems include those described in U.S. Pat. No. 4,160,997 to Robert Schwartz and U.S. Pat. No. 5,434,418 to David Schick. Filmless dental radiography systems typically utilize a standard desktop computer, such as an IBM or IBM compatible type personal computer.

SUMMARY OF THE PRESENT INVENTION

The present invention provides an intraoral sensor configured to fit comfortably and close to a target area in an intraoral cavity. By providing a comfortable relative to the target area, the sensor is ergonomically improved, in terms of its comfort and feel to a dental patient. Whereas prior sensors had housings that were generally rectangular and flat (particularly in cross section), the sensor of the present invention has a predetermined curvature in any plane through the sensor. Thus, certain surfaces of the sensor have non zero curvatures, as described more fully herein. This makes the sensor more comfortable for a patient in comparison to the prior sensors.

In addition, the preferred configuration of the sensor is designed to allow the sensor to be placed closer to a target area in an oral cavity than prior sensors (i.e. closer to target teeth, gum, etc). Moreover, the sensor is configured so that it can easily be located in a correct position relative to the target area, and when located correctly to properly position its sensing structure for receiving radiant energy. These features are believed to reduce refractive error in the image received by the sensor, thereby improving the image data transmitted by the sensor.

Still further, the preferred configuration of the sensor is relatively thin, which also contributes to the improved ergonomics of the sensor, and enables the sensor to get closer to the target area of an oral cavity, thereby improving the image data transmitted by the sensor.

Further features of the present invention will become apparent from the following detailed description taken with reference to the accompanying drawings.

BRIEF DESCRIPTION OF THE DRAWINGS

FIG. 1 is a top right perspective view of a sensor according to the present invention;

FIG. 2 is a bottom left perspective view of the sensor of FIG. 1;

FIG. 3 is a front view of the sensor of FIG. 1, projected from the right side of FIG. 7;

FIG. 4 is a rear view of the sensor of FIG. 1, projected from the left side of FIG. 7;

FIG. 5 is a top view of the sensor of FIG. 1;

FIG. 6 is a bottom view of the sensor of FIG. 1;

FIG. 7 is a right side view of the sensor of FIG. 1, (the left side view being a mirror image of FIG. 7)

DETAILED DESCRIPTION

Figure 9:
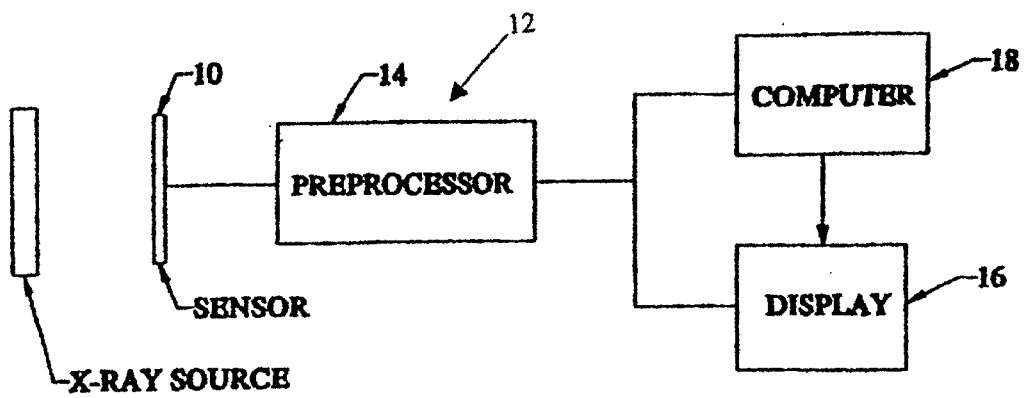
FIG. 9 is a schematic representation of a filmless radiography system using a sensor according to the present invention.

A sensor according to the present invention is designed to be used with a filmless radiography system. As an example, a sensor 10 according to the present invention can be used as part of a filmless radiography system 12 (FIG. 9) which is designed according to the principles of Schwartz U.S. Pat. No. 4,160,997 (Schwartz patent), which is incorporated herein by reference. As illustrated in FIG. 9, the sensor 10 transmits digital image data to a preprocessor 14, and the preprocessor transmits the image data either directly to a display device 16, or to a computer 18 which is connected to the display device 16. The preprocessor 14 is configured to normalize the image data transmitted by the sensor 10, to improve the contrast (color and/or grayscale) of such data in relation to the raw image data produced by the sensor. The image data is then transmitted directly to the display device 16, or the image data is transmitted to the computer 18 which can manipulate the image data on the display device. The manner in which the image is processed, transmitted and/or displayed can be in accordance with the principles of the Schwartz patent, or in accordance with other well known devices and systems for processing and displaying the image data. Such devices and systems are well known to those in the art and should not require further explanation.

Figure 8:
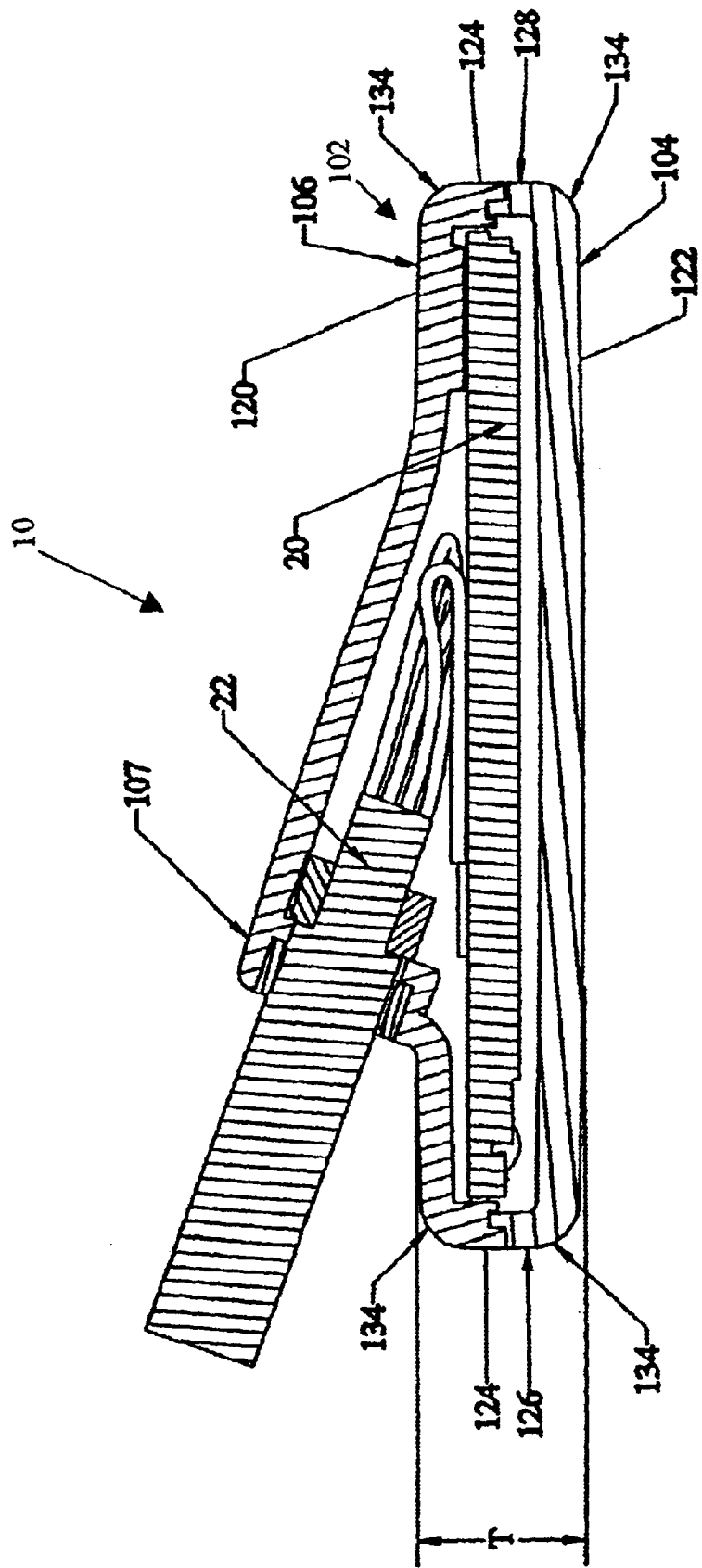
FIG. 8 is sectional view of the sensor, taken from the direction 8—8 in FIG. 5, further illustrating a section for connecting the sensor to a processing system.

In addition, the sensor 10 has internal structure, schematically illustrated at 20 in FIG. 8, which is designed in accordance with the principles of the Schwartz patent. The internal structure 20 includes components which receive radiated energy image data from a target area of an intraoral cavity (e.g. x-ray images of a patient's teeth, gums, etc), convert the resulting x-ray image data into a visible light image, and transmit the visible light image to a charge coupled device (CCD) or any other visible light sensor forming part of the structure 20. For example, the internal structure 20 could include an array of CCD detectors, a printed circuit board associated with the CCD detectors, a radiant energy screen with a phosphor coating to convert a radient energy image to a visible image that impinges on the CCD detectors. The printed circuit board is coupled to a cable 22 which transmits the image data from the CCD array to the preprocessor 14 which preprocesses and transmits the image data to the display device 16 and/or to the computer 18. Again, the internal structure 20 of the sensor can be constructed in various known ways, and should not require further explanation to those in the art.

The basic configuration for an intraoral sensor 10 according to the present invention is disclosed in FIGS. 1–8. In FIGS. 1–8, the sensor comprises a sensor body (or housing) 102 configured to fit in a patient's oral cavity proximate a target area of the oral cavity. The sensor body 102 has two sections, a lower section 104, and an upper section 106. The lower section 104 can be formed e.g. from a biocompatible carbon material that is transparent to x-ray energy. The upper section 106 can be formed, e.g from a biocompatible thermoplastic material. The upper and lower sections are bonded or otherwise fastened together, and enclose the sensing device 20 shown in FIG. 8. The upper section 106 is configured with a cable connector 107, which enables receives the electrical cable 22 that connects to the printed circuit board of the sensing structure 20 (see FIG. 8).

Also, while the lower section 104 of the sensor body is black, the upper section 106 of the sensor body is a color other than black (e.g. one preferred color for the upper section is blue). The color contrast between the upper and lower sections enables the sensor to be easily located in a proper position in an oral cavity, as described further below. Moreover, as seen in FIG. 8, the sensing structure 20 is oriented to receive x-rays that are directed through the lower section 104 at about 90° to the direction of the x-rays, for reasons also explained more fully below.

In accordance with the present invention, the external surface of the sensor body is configured with a predetermined curvature in any plane extending through the sensor body. In other words, in any plane which cuts through the sensor body 102, the external surface will have portions that have predetermined curvatures. Thus, certain surfaces of the sensor have non zero curvatures, as described further below.

As illustrated in FIGS. 1–8 the upper and lower portions of the sensor body have respective upper and lower surfaces 120, 122 and an intermediate surface 124 extends between the upper and lower surfaces 120,122. Each of the upper, lower and intermediate surfaces has a predetermined curvature. The curvatures of the upper and lower surfaces 120,122 are non-zero and are configured such that the upper and lower surfaces curve away from each other (see e.g. FIGS. 3,4,7). Also, the intermediate surface has 2 pairs of opposite sides (one pair shown at 126, 128; the other pair shown at 130,132). As illustrated in the Figures, each pair of opposite sides has a non zero curvature such that each pair of opposite sides curve away from each other. The intermediate surface 124 also has corner portions 134 which extend between the upper surface 120 and respective portions of each pair of opposite sides (126,128; 130,132) of the intermediate surface, and between the lower surface 122 and respective portions of each pair of opposite sides (126,128; 130,132) of the intermediate portion.

As illustrated in FIG. 8, according to the preferred embodiment each of the larger and smaller versions of the sensor has a maximum thickness T (not including the cable connector 107) of about 5 mm (0.215 inches). The larger version of the sensor has a maximum length of about 1.703 inches, and a maximum width of about 1.338 inches The smaller version of the sensor has a maximum length of about 1.463 inches, and a maximum width of about 1.043 inches. Thus, the larger and smaller versions of the sensors have a generally similar configuration, and differ primarily in their respective sizes (lengthwise and widthwise), color of their upper sections, and in the specific curvatures of their surfaces (on account of their differences in length and width). However, each sensor is configured such that there is a predetermined curvature in any plane through the sensor.

Figure 10:
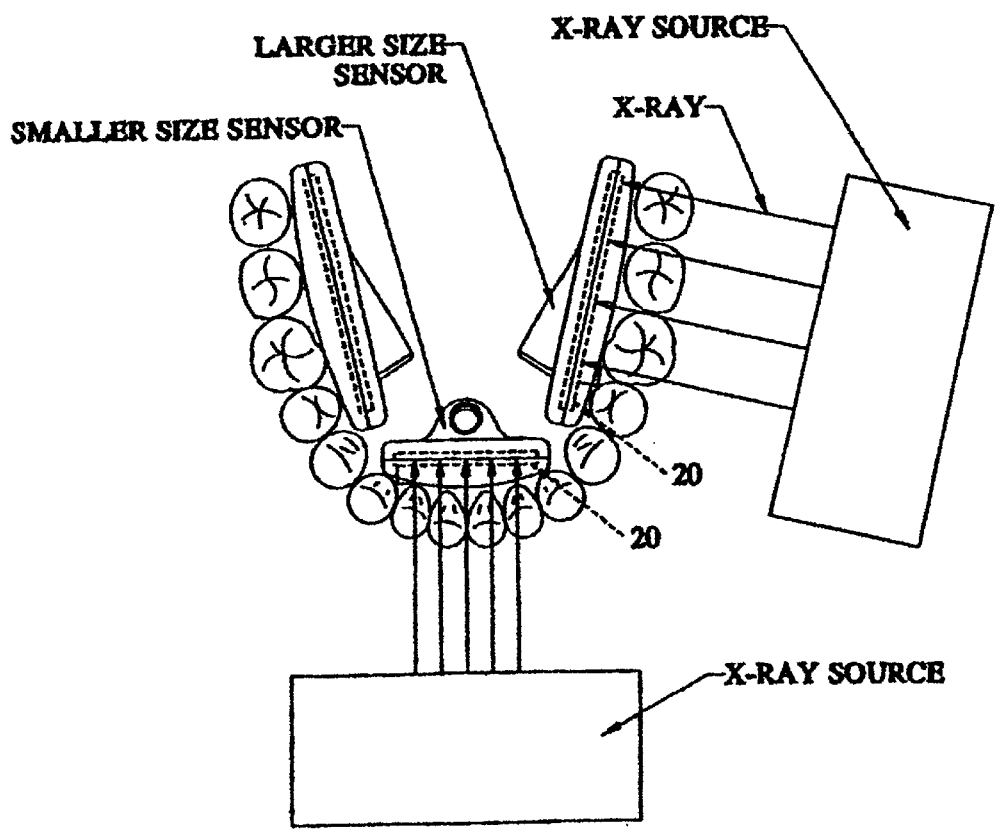
FIG. 10 schematically illustrates exemplary positions for sensors according to the present invention in an intraoral cavity.

FIG. 10 schematically illustrates exemplary positions for both larger and smaller versions of a sensor according to the present invention in relation to target areas of a patient's intraoral cavity. In FIG. 10, the target areas are groups of the patient's teeth, but those target areas could be individual teeth, or portions of the patient's gums (or any other area of a patient's mouth for which it is desirable to capture an image by an x-ray). In FIG. 10 the smaller version of the sensor is located at a target area at the front of the patient's mouth, and larger versions are located at target areas to the sides of the patient's mouth. As seen from FIG. 10, the curvatures of the surfaces of the sensor enable the sensors to fit comfortably and close to the target areas of the patient's mouth. The contrasting colors of the upper and lower sections of the sensor body enables the sensor to be properly positioned in a patient's mouth (i.e. the black lower section is always positioned adjacent the target area). Moreover, the sensing structure 20 is positioned in the sensor body 102 so that when the sensor is properly positioned relative to a target area, the sensing structure will receive x-ray energy at about 90° to the direction of the x-ray energy. By providing a comfortable fit relative to the target areas, the sensors are ergonomically improved, in terms of its comfort and feel to a dental patient. In addition, the configuration of the sensor is designed to allow the sensor to be placed closer to a target area in an oral cavity than prior sensors (i.e. closer to target teeth, gum, etc). This feature, and the fact that when the sensor is properly positioned relative to a target area the x-ray energy will by received by the sensing structure 20 at about 90° to the direction of the x-rays is believed to reduce refractive error in the image received by the sensor, thereby improving the image data transmitted by the sensor. Still further, the preferred embodiment of the sensor is relatively thin (e.g. with a thickness of about 5 mm), which also contributes to the improved ergonomics of the sensor, and enables the sensor to get closer to the target area of an oral cavity, thereby improving the image data transmitted by the sensor.

Accordingly, the foregoing disclosure provides a sensor configuration which is particularly useful as a filmless radiography sensor. With the foregoing disclosure in mind, the manner in which the principles of the invention can be used to form various types of intraoral sensors for various uses comparable to filmless radiography will be apparent to those in the art.

What is claimed is:

1. An intraoral sensor comprising a sensor body configured to fit in an oral cavity proximate a target area of the oral cavity, said sensor body housing filmless radiation sensing structure, the sensor body having upper and lower surfaces and an intermediate surface extending between said upper and lower surfaces, said lower surface having a non zero curvature and being configured to curve away from said upper surface, and said intermediate surface including two pairs of opposite sides, each opposite side having a non zero curvature and being configured such that each pair of opposite sides curve away from each other.

2. An intraoral sensor as defined in claim 1, wherein said intermediate surface has corner portions which extend between the upper surface and respective portions of each pair of opposite sides of the intermediate surface, and between the lower surface and respective portions of each pair of opposite sides of the intermediate portion.

3. An intraoral sensor as defined in claim 2, wherein said sensor body has a thickness of about 5 mm.

4. An intraoral sensor comprising a sensor body configured to fit in an oral cavity proximate a target area of the oral cavity, said sensor body comprising upper and lower sections and sensing structure disposed between said upper and lower sections; said upper and lower sections having contrasting colors and respective external surfaces with non zero curvatures to enable the sensor to be properly positioned relative to a target area, and said sensing structure being oriented in said sensor body such that when said sensor is properly positioned relative to a target area said sensing structure will receive radiant energy at a predetermined orientation relative to the direction of the radiant energy.

* * * * *